(12) United States Patent
Hausen et al.

(10) Patent No.: US 7,730,889 B1
(45) Date of Patent: Jun. 8, 2010

(54) FALLOPIAN TUBE OCCLUSION SYSTEM

(75) Inventors: Bernard A. Hausen, Redwood City, CA (US); Luke W. Clauson, Redwood City, CA (US)

(73) Assignee: Cardica, Inc., Redwood City, CA (US)

( * ) Notice: Subject to any disclaimer, the term of this patent is extended or adjusted under 35 U.S.C. 154(b) by 50 days.

(21) Appl. No.: 12/140,967

(22) Filed: Jun. 17, 2008

(51) Int. Cl.
*A61F 6/06* (2006.01)
*A61B 17/10* (2006.01)
*A61M 29/00* (2006.01)

(52) U.S. Cl. .................. 128/831; 606/141; 606/193
(58) Field of Classification Search .................. 128/830, 128/831, 832, 833, 838, 898; 600/29, 30, 600/31, 434; 606/139, 141, 144, 148, 153, 606/157–158, 191, 193, 194, 198, 197, 196
See application file for complete search history.

(56) References Cited

U.S. PATENT DOCUMENTS 5,935,137 A * 8/1999 Saadat et al. ................. 606/135

6,736,822 B2 * 5/2004 McClellan et al. .......... 606/139
2005/0187561 A1 * 8/2005 Lee-Sepsick et al. ........ 606/108

\* cited by examiner

*Primary Examiner*—Patricia M Bianco
*Assistant Examiner*—Ophelia Hawthorne
(74) *Attorney, Agent, or Firm*—Brian A. Schar

(57) ABSTRACT

An implantable sterilization device may include a ring having an inner diameter, a core slidable through the inner diameter of the ring, and a tissue securing element, at least part of which is positioned between the ring and the core. A method of closing a fallopian tube may include providing a closure system including a handle, a flexible shaft connected to the handle, and a sterilization device detachably connected to the flexible shaft, inserting the flexible shaft into the lumen of the fallopian tube and advancing the flexible shaft into the lumen; compressing a portion of the wall of the fallopian tube with the sterilization device to secure the sterilization device relative to the fallopian tube, blocking the lumen of the fallopian tube with the sterilization device; and separating the sterilization device from the tube.

18 Claims, 4 Drawing Sheets

FALLOPIAN TUBE OCCLUSION SYSTEM

FIELD OF THE INVENTION

The invention generally relates to a surgical tool and method, and more specifically to a surgical tool and method for occluding a fallopian tube.

BACKGROUND

At the present time, satisfactory options for female birth control are limited. Nonsurgical methods such as birth control pills and other pharmaceutical solutions rely on the user to remember to take the medication. Further, pharmaceuticals are simply unaffordable or inaccessible to many women around the world. The most common surgical method for female birth control is tubal ligation. While effective, this surgery is highly invasive, painful, and cosmetically undesirable. Although less invasive surgical techniques and devices have been proposed for female sterilization, they have generally proven either disastrous (for example, the intrauterine device (IUD)) or less than optimally effective. The more successful systems attempt to close the fallopian tube, but require tissue ingrowth into a coil or other device, or growth of scar tissue as a result of treatment with heat, cold, RF or chemicals, such that sterilization follows the procedure several months later at a time that is not known to the patient. That is, sterilization is not immediate, but instead relies on the healing response of the body. Further, an invasive diagnostic procedure to confirm closure may be required.

BRIEF DESCRIPTION OF THE DRAWINGS

The use of the same reference symbols in different figures indicates similar or identical items.

DETAILED DESCRIPTION

Closure System

Figure 1:
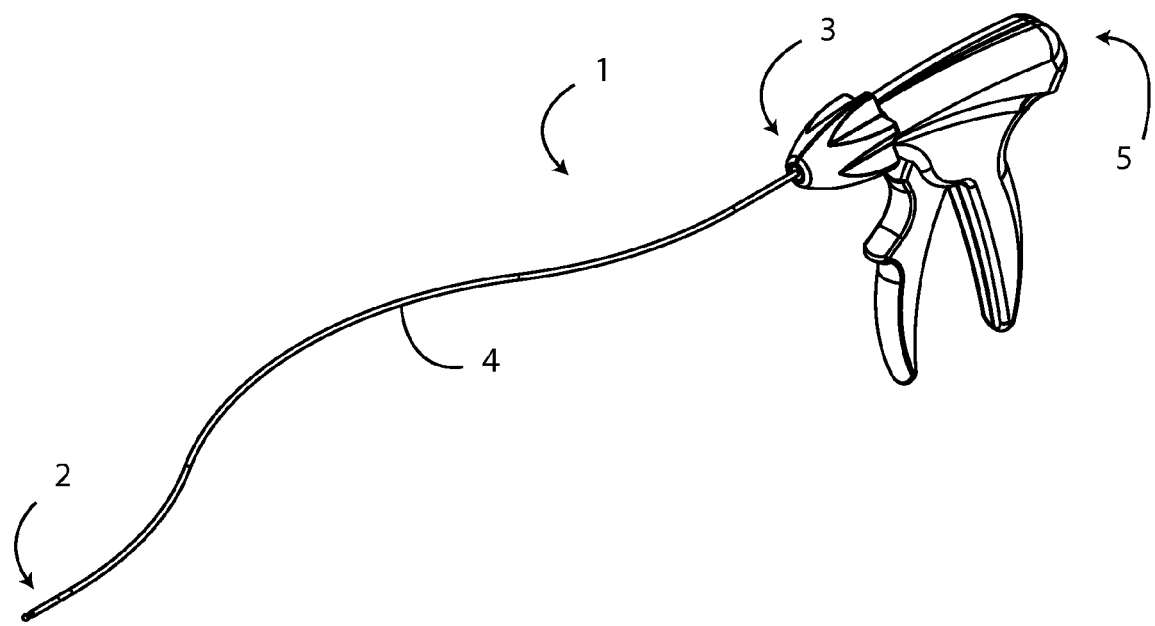
FIG. 1 is a perspective view of a closure system that includes a deployment mechanism and a sterilization device.
Figure 2:
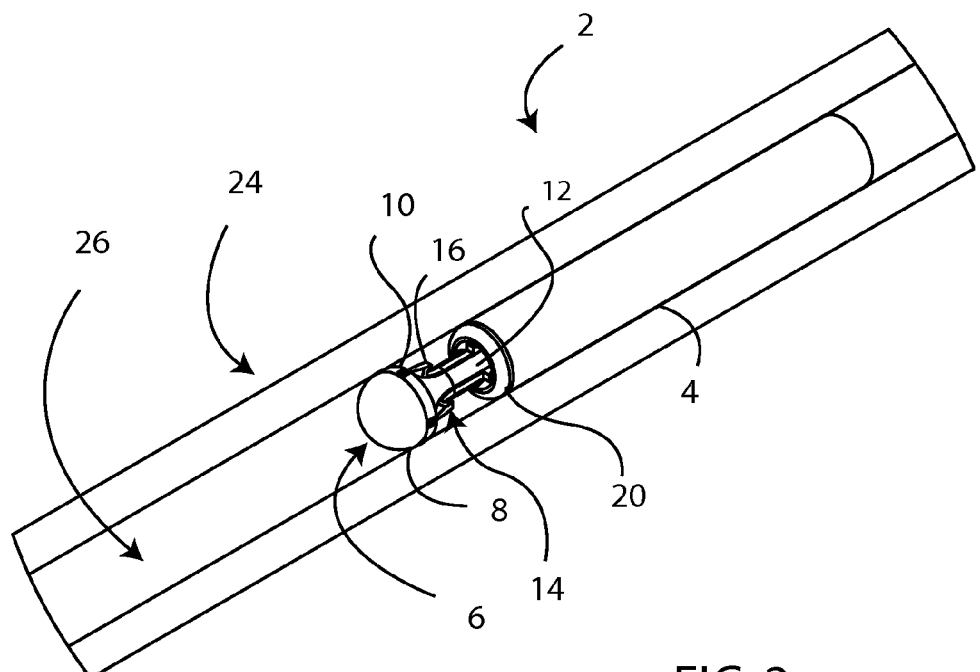
FIG. 2 is a perspective cutaway view of the sterilization device in a first configuration.

Referring to FIGS. 1-2, a closure system 1 may include an implantable sterilization device 2 connected to a deployment mechanism 3. The deployment mechanism 3 includes a flexible tube 4 that has a lumen defined longitudinally therethrough. The tube 4 advantageously has an outer diameter of two millimeters or less, such that the tube 4 may be received easily in both a fallopian tube and in the working channel of a conventional endoscope. However, the tube 4 may have any other suitable diameter. The tube 4 extends between the sterilization device 2 and the handle 5 of the deployment mechanism 3. The handle 5 may be a standard trigger grip, or may be configured in any other suitable manner. The sterilization device 2 is actuable by and separable from the deployment mechanism 3 in any suitable manner, as described in greater detail below.

Figure 5:
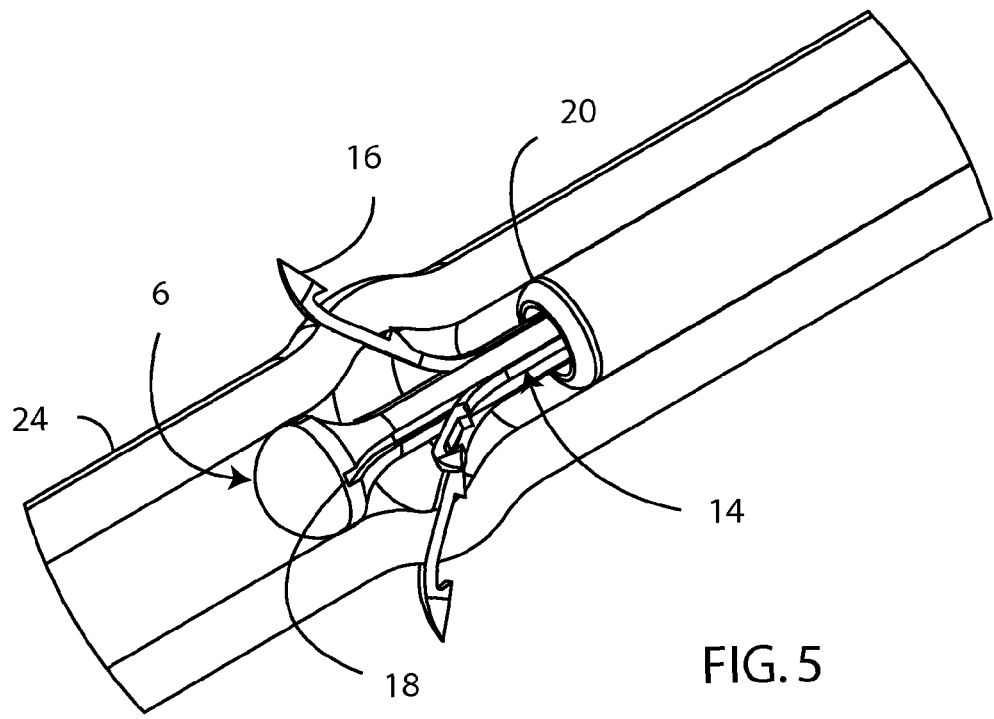
FIG. 5 is a perspective cutaway view of the sterilization device in a third configuration.
Figure 8:
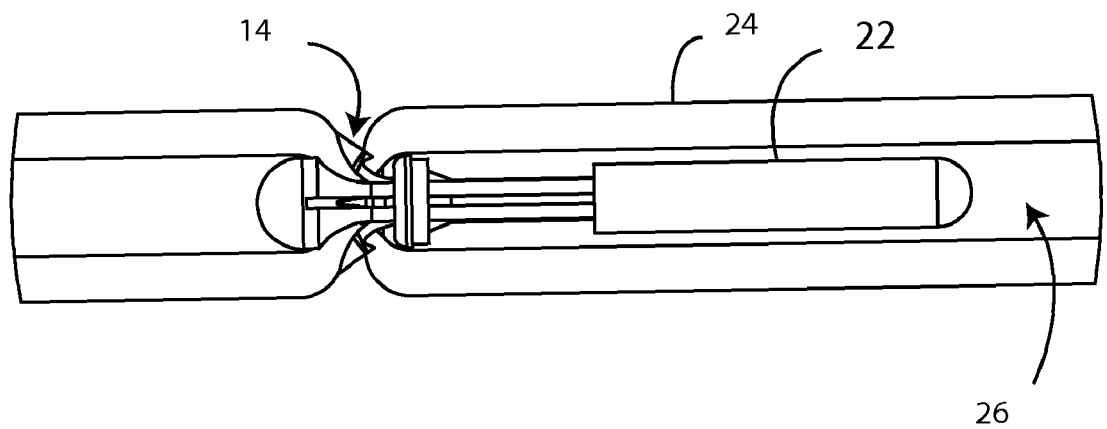
FIG. 8 is a side cutaway view of the sterilization device in the fifth configuration, after its release from the deployment mechanism.

Referring to FIG. 2, the sterilization device 2 is shown in a first, predeployment configuration. The sterilization device 2 includes a ring 20 that is held by the tube 4 of the deployment mechanism 3. Referring also to FIG. 8, at least part of the ring 20 may extend distally outward from the tube 4. Alternately, the ring 20 may be held completely within the tube 4, or may be positioned completely outside the tube 4. The tube 4 may retain the ring 20 in any suitable manner, such as by a friction fit. The ring 20 may be detachably connected to the tube 4. The sterilization device 2 may include a core 6 that extends distally outward from the tube 4. The core 6 may be configured in any suitable manner. As one example, the core 6 includes an atraumatic tip 8 located distal to the tube 4, and a shaft 12 extending proximally into the lumen of the tube 4. The atraumatic tip 8 may be curved in a hemispherical or other convex manner, coated in atraumatic material, or otherwise configured such that advancement of the distal end of the core 6 through the fallopian tube does not substantially engage or damage tissue of the fallopian tube. The atraumatic tip 8 is advantageously two millimeters in diameter or less, such that the atraumatic tip 8 can be received easily in both a fallopian tube and in the working channel of a conventional endoscope. However, the atraumatic tip 8 may have any other suitable diameter, and/or any other suitable shape or profile. Proximal to the atraumatic tip 8, the core 6 may include a deformation surface 10 that may be curved in a concave manner and decrease smoothly in diameter along the proximal direction. Alternately, the deformation surface 10 of the core 6 may be shaped in any other suitable manner. Referring also to FIG. 5, one or more channels 18 may be defined in the deformation surface 10. The channels 18 may extend generally longitudinally and may have a generally rectangular cross section. The channels 18 may be generally evenly spaced along the circumference of the deformation surface 10. Alternately, the channels 18 may be spaced, shaped, oriented and/or configured differently, or omitted altogether. Referring also to FIG. 2, proximal to the deformation surface 10, the core 6 may include a shaft 12 that may have a generally constant diameter. The shaft 12 may extend into the lumen of the tube 4.

The sterilization device 2 includes a tissue control element 14 that may be configured in any suitable manner. As one example, the tissue control element 14 may include a plurality of tines 16 with sharpened distal ends, where those tines 16 extend in the proximal direction into the tube 4. The tines 16 may be connected to one another, or at least one tine 16 may be independent of the others. The tines 16 may be oriented such that their distal ends are initially positioned on or adjacent to the deformation surface 10, proximal to the atraumatic tip 8. However, the tines 16 may be configured and/or oriented in any other suitable manner. At least part of at least one tine 16 may be held within a corresponding channel 18 on the deformation surface 10. The tissue control element 14 may be fabricated from any suitable biocompatible material, such as stainless steel, nickel-titanium alloy, or a nonmetallic material. The tissue control element 14 may be plastically deformable, elastically deformable, superelastically deformable, or otherwise deformable. As another example, the tissue control element 14 may be fixed to the core 6, and include tines 16 oriented generally proximally. If so, the tines 16 may be fixed to the deformation surface 10. As another example, the tissue control element 14 may omit the tines 16 and assume another configuration. As another example, the tissue control element 14 may be omitted from the sterilization device 2.

Referring also to FIG. 8, the tines 16 of the tissue control element 14, and/or a portion of the tissue control element 14 connected to the tines 16, may extend proximally through the ring 20. The tines 16 and/or other portion of the tissue control element 14 may be fixed to the ring 20, compressed by the ring 20, or otherwise associated with the ring 20. Optionally, the tines 16 and/or other portion of the tissue control element 14 that extend proximal to the ring 20 may continue proximally until terminating at or within a cap 22. The tines 16 and/or other portion of the tissue control element 14 may be connected to the cap 22 in any suitable manner, such as by molding, by friction fit, by adhesive or by welding. The cap 22 may be spaced apart from and located proximal to the ring 20. The cap 22 may be positioned at a substantially fixed distance relative to the ring 20. Alternately, the ring 20 and cap 22 may be parts of a continuous assembly during part or all of the deployment of the sterilization device 2.

Operation

To begin the procedure, a standard endoscope may be introduced through the patient's cervix into the uterus, such that the distal end of the endoscope is placed in a position to view the junction of the cervix and uterus. Referring to FIG. 1, the sterilization device 2 and part of the tube 4 are then advanced through the patient's cervix into the uterus, and then into the fallopian tube. Advantageously, the sterilization device 2 and part of the tube 4 are advanced into the fallopian tube through the working channel of the endoscope. However, the closure system 1 may be utilized with an endoscope that does not have a working channel, such that the sterilization device 2 is advanced into the fallopian tube outside of the endoscope. As another example, an endoscopic viewing system may be integrated with the sterilization device 2. Optionally, one or more indicia may be defined on the tube 4 to provide feedback to the user as to the depth of insertion of the tube 4 into the fallopian tube. Such indicia may include one or more visible lines on the surface of the tube 4, one or more radio-opaque structures placed in or on the tube 4, or any other suitable indicia. The user may view the indicia via the endoscope, a fluoroscope or other viewing device, such that the tube 4 may be advanced into the fallopian tube until a particular indicia reaches the junction between the fallopian tube and the uterus. The atraumatic tip 8 of the core 6 at the distal end of the sterilization device 2 substantially minimizes damage to the interior of the fallopian tube 24 as the sterilization device 2 moves through the lumen 26. After the sterilization device 2 has been moved to the desired position within the lumen 26 of the fallopian tube 24, motion of the sterilization device 2 stops.

Figure 3:
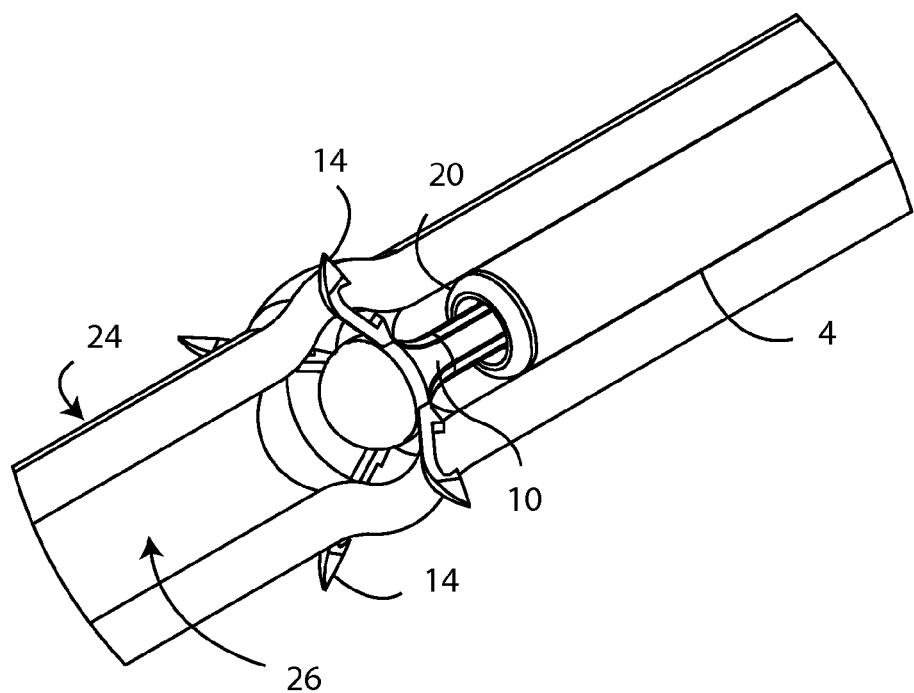
FIG. 3 is a perspective cutaway view of the sterilization device in a second configuration.
Figure 4:
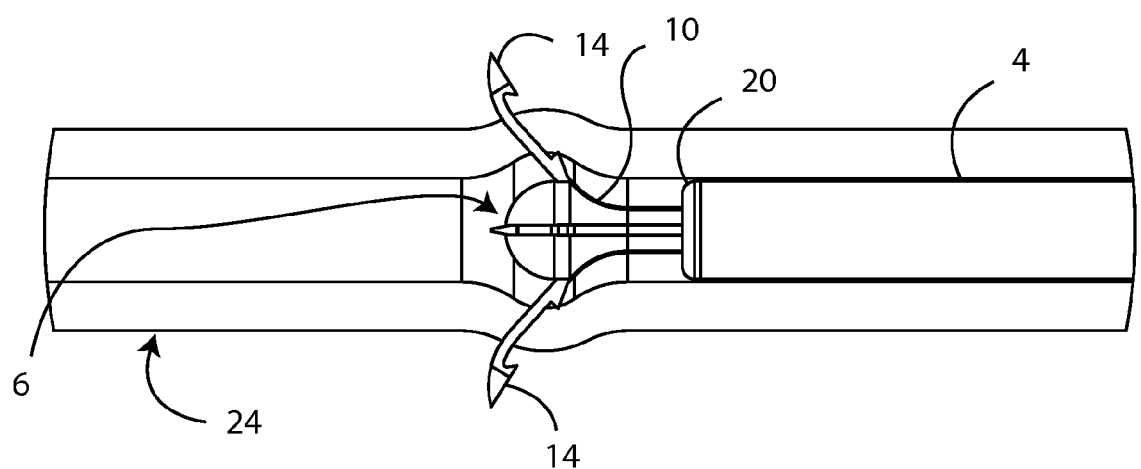
FIG. 4 is a side cutaway view of the sterilization device in the second configuration.

Referring also to FIG. 2, the sterilization device 2 is in an initial position when it moves into the lumen 26 of the fallopian tube 24. In that initial position, the distal end of the sterilization device 2 is spaced apart from the ring 20 by a first distance. Referring also to FIG. 1, the user then actuates the handle 5 of the deployment mechanism 3. As described above, the handle 5 may include a trigger grip, knob, and/or any other suitable actuation mechanism. Referring also to FIGS. 3-4, as the user actuates the handle 5, the tissue control element 14 is urged distally in any suitable manner. As one example, a cable (not shown) or other force transmission element extends through the lumen of the tube 4 and engages the tissue control element 14. As another example, the tissue control element 14 itself may extend along the lumen of the tube 4 to the handle 5, where the tissue control element 14 is later frangible at or near the boundary of the sterilization device 2 to allow separation of the sterilization device 2 from the closure system 1. Distal motion of the tissue control element 14 urges the tines 16 against the deformation surface 10 of the core 6. Advantageously, referring also to the view of the core 6 seen in FIG. 5 without reference to its position in that figure, one or more of the tines 16 slide along a corresponding channel 18 defined in the deformation surface 10. Each channel 18 guides the corresponding tine 16 in a desired direction relative to the core 6. As each tine 16 moves distally along the deformation surface 10, the curvature of the deformation surface 10 causes the distal end of that tine 16 to move at least in part in a direction away from the longitudinal centerline of the sterilization device 2 and into the tissue of the wall of the fallopian tube 24, and then penetrate the wall of the fallopian tube 24. As used in this document, the words "penetrate," "penetrates" and "penetration" are defined to mean motion of a structure completely through the wall of the fallopian tube 24. Alternately, at least one tine 16 enters partially into the wall of the fallopian tube 24 but does not penetrate the wall of the fallopian tube 24. Alternately, where the tissue control element 14 does not utilize tines 16, the tissue control element 14 is otherwise deformed against the deformation surface 10 of the core 6 upon actuation of the handle 5, and may or may not penetrate the wall of the fallopian tube 24. Alternately, the tissue control element 14 is otherwise deformed or manipulated upon actuation of the handle 5.

Figure 6:
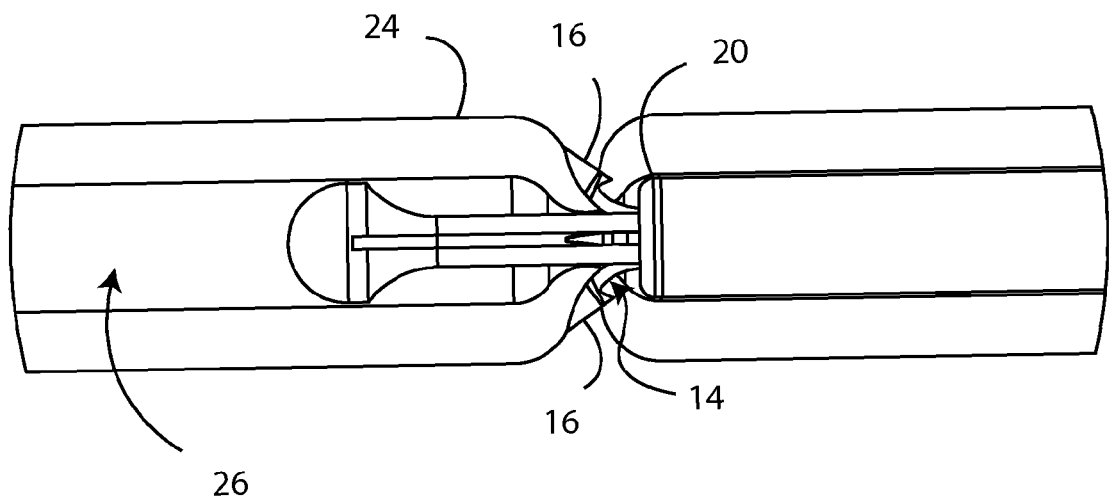
FIG. 6 is a perspective cutaway view of the sterilization device in a fourth configuration.

Next, referring also to FIG. 5, as the user continues to actuate the handle 5, the core 6 is advanced distally relative to the ring 20 and the tissue control element 14 in any suitable manner. As one example, a force transmission element (not shown) extends through the lumen of the tube 4 and engages the shaft 12 of the core 6 to urge the core 6 distally. As another example, the shaft 12 itself may extend along the lumen of the tube 4 to the handle 5, where the shaft 12 is later frangible at or near the boundary of the sterilization device 2 to allow separation of the sterilization device 2 from the closure system 1. The tines 16 may flex or move inward toward the longitudinal centerline of the fallopian tube 24 as a result, or may remain in their previous position. The tines 16 may remain in a location in which at least one tine 16 penetrates the wall of the fallopian tube 24. Next, referring also to FIG. 6, the tissue control element 14 is retracted proximally. As a result, the tissue control element 14 pulls the wall of the fallopian tube 24 inward, reducing the diameter of the lumen 26. Where the tissue control element 14 includes one or more tines 16, the distal end of each tine 16 may be notched, configured in a fishhook-like manner, or otherwise configured such that retraction of each tine 16 causes the tines 16 to engage the outer surface of the wall of the fallopian tube 24 and draw that wall inward, instead of slipping out of the wall of the fallopian tube 24. As the tines 16 are retracted, the distance between the distal end of each tine 16 and the ring 20 decreases, such that tissue of the wall of the fallopian tube 24 may be compressed longitudinally and bunched between the tines 16 and the ring 20. Alternately, the tissue control element 14 may draw the wall of the fallopian tube 24 inward and/or compress it in any suitable manner, or may not draw the wall of the fallopian tube 24 inward and/or compress it at all.

Figure 7:
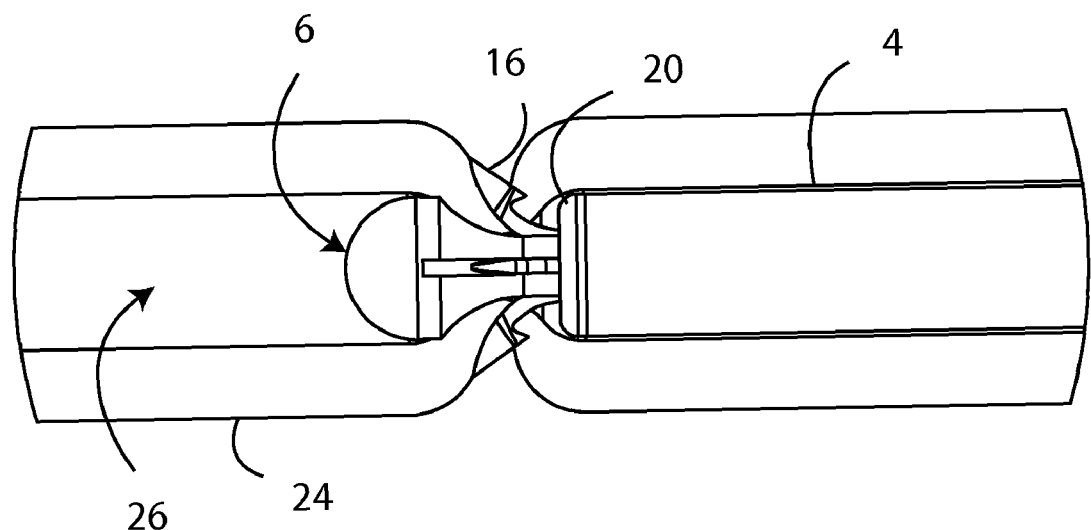
FIG. 7 is a perspective cutaway view of the sterilization device in a fifth configuration.

Next, referring also to FIG. 7, the core 6 is retracted proximally toward the ring 20, such that the distance between the core 6 and the ring 20 decreases. The core 6 may move proximally until it ceases motion relative to the ring 20, in a final position. In the final position, the core 6 may be locked into place relative to the ring 20. Such locking may be accomplished in any suitable manner. As one example, the core 6 varies in diameter along its length, such that retraction of the core 6 causes a portion of the core 6 having a diameter substantially the same as the opening in the ring 20 to enter the ring 20 and thereby lock the core 6 in place by a friction and/or interference fit. As another example, a locking feature (not shown) may be included on the core 6, ring 20 and/or cap 22, such that retraction of the core 6 causes engagement between locking features, or between a locking feature and the core 6, ring 20 and/or cap 22. As described above, tissue of the wall of the fallopian tube 24 already may be bunched between the tines 16 and the ring 20 before proximal motion of the core 6. When the core 6 is in the final position, the distal end of the core 6 and the ring 20 may compress that bunched tissue further, and/or simply hold that bunched tissue in place. Alternately, the tissue of the fallopian tube 24 has not been compressed substantially beforehand, and motion of the distal end of the core 6 toward the ring 20 causes such compression. Compression of the tissue of the fallopian tube 24 secures the sterilization device 2 in place in the fallopian tube 24. The sterilization device 2 is now in the closed position, in which the distal end of the sterilization device 2 is spaced apart from the ring 20 by a second distance that is less than the first distance. The walls of the fallopian tube 24 have been pulled inward toward the core 6, bunched together, and locked in place, and the core 6 blocks the lumen 26 of the fallopian tube 24.

At this time, the user may test to ensure that the sterilization device 2 is locked in place, by gently pulling on the tube 4 in the proximal direction. If the tube 4 does not substantially move, then the sterilization device 2 is locked in place, and the patient is sterilized. The closure of the fallopian tube 24 is immediate, and does not depend on a healing response from the tissue of the fallopian tube 24. If the tube 4 does move, then the sterilization device 2 has not been locked in place, and may be withdrawn from the fallopian tube 24, after which the user may try again with the same or a different closure system 1. Referring also to FIG. 8, the tube 4 is then separated from the sterilization device 2, leaving the sterilization device 2 in place in the fallopian tube 24. The tube 4 may be separated from the sterilization device 2 in any suitable manner. As one example, the tube 4 is friction fit or interference fit to the cap 22, such that a known force overcomes that fit and causes the tube 4 to separate from the cap 22, where the known force is at least equal to the force that securely holds the sterilization device 2 permanently in place in the fallopian tube 24. Such a disconnection may be referred to as a passive disconnection. Alternately, the sterilization device 2 may be disconnected from the tube 4 in any other suitable manner. The procedure is then complete.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A method of closing a fallopian tube having a wall encircling a lumen, comprising:
   providing a closure system including a handle, a flexible shaft connected to said handle, and a sterilization device detachably connected to said flexible shaft; said sterilization device including a ring having an inner diameter, a core slidable through said inner diameter of said ring, wherein said core includes a deformation surface defined thereon, and a tissue securing element, at least part of which is positioned between said ring and said core, wherein said tissue securing element includes a plurality of tines with sharpened distal ends configured to penetrate the wall of the fallopian tube;
   inserting said flexible shaft into the lumen of the fallopian tube and advancing said flexible shaft into the lumen of the fallopian tube;
   penetrating said tines outward through the wall of the fallopian tube;
   retracting said tines toward said core;
   compressing a portion of the wall of the fallopian tube with said sterilization device to secure said sterilization device relative to the fallopian tube;
   locking said core into place with said ring to maintain said compressing;
   blocking the lumen of the fallopian tube with said sterilization device; and
   separating said sterilization device from said tube.

2. The method of claim 1, incorporating by reference all of the limitations of that claim, wherein the sterilization device includes a tissue securing member; further comprising penetrating the wall of the fallopian tube with at least part of the tissue securing member.

3. The method of claim 2, incorporating by reference all of the limitations of that claim, further comprising a core having a distal end and a ring located proximal to the distal end of the core; wherein at least part of the tissue securing member is located between the distal end of the core and the ring; wherein the compressing comprises moving the distal end of the core proximally toward the ring.

4. The method of claim 3, incorporating by reference all of the limitations of that claim, further comprising moving at least part of the tissue securing member inward and proximally toward the ring after the penetrating.

5. The method of claim 2, incorporating by reference all of the limitations of that claim, wherein the tissue securing member includes a plurality of tines, and wherein the penetrating comprises penetrating the wall of the fallopian tube with at least one the tine.

6. The method of claim 1, incorporating by reference all of the limitations of that claim, further comprising providing an endoscope and viewing the inserting with the endoscope.

7. The method of claim 6, incorporating by reference all of the limitations of that claim, wherein the endoscope includes a working channel; further comprising inserting the flexible shaft through the working channel.

8. The method of claim 6, incorporating by reference all of the limitations of that claim, wherein the flexible shaft includes at least one indicia, and wherein the depth of the inserting into the lumen of the fallopian tube is controlled based on observation of the indicia.

9. An implantable sterilization device for placement in the fallopian tube of a patient, that tube having a wall encircling a lumen, comprising:

a ring having an inner diameter;

a core slidable through said inner diameter of said ring, wherein said core includes a deformation surface defined thereon; and a tissue securing element, at least part of which is positioned between said ring and said core, wherein said tissue securing element includes a plurality of tines with sharpened distal ends configured to penetrate the wall of the fallopian tube;

wherein said tissue securing element is movable relative to said core to cause at least the distal ends of said tines to move outward away from said core completely through the wall of the fallopian tube, and then said tissue securing element is movable inward toward said core to grasp the wall of the fallopian tube from outside; and wherein said core is movable proximally relative to said ring to compress a portion of the wall of the fallopian tube between said core and said ring, and wherein said core locks into place with said ring to maintain compression of the wall of the fallopian tube between said core and said ring.

10. The device of claim 9, incorporating by reference all of the limitations of that claim, further comprising a cap positioned proximal to said ring, wherein part of said tissue securing element extends through said inner diameter of said ring and connects to said cap.

11. The device of claim 10, incorporating by reference all of the limitations of that claim, wherein said cap is spaced apart from said ring at a substantially fixed distance.

12. The device of claim 9, incorporating by reference all of the limitations of that claim, wherein said core includes a generally concave deformation surface that decreases in diameter along the proximal direction.

13. The device of claim 12, incorporating by reference all of the limitations of that claim, wherein said tissue securing element includes a plurality of tines configured to move outward from the longitudinal centerline of said core upon contact with said deformation surface.

14. The device of claim 9, incorporating by reference all of the limitations of that claim, wherein said tissue securing element includes a plurality of tines.

15. The device of claim 9, incorporating by reference all of the limitations of that claim, wherein said core includes a longitudinally-extending shaft, a segment of which has an outer diameter at least as wide as said inner diameter of said ring.

16. The device of claim 9, incorporating by reference all of the limitations of that claim, further comprising a plurality of channels defined in said deformation surface, wherein each said channel receives part of said tissue securing element.

17. The device of claim 9, incorporating by reference all of the limitations of that claim, wherein the distal end of said core is atraumatic.

18. The device of claim 9, incorporating by reference all of the limitations of that claim, wherein a portion of said tissue securing element is slidable through said inner diameter of said ring.

\* \* \* \* \*